(12) United States Patent
Brady

(10) Patent No.: US 8,021,702 B2
(45) Date of Patent: Sep. 20, 2011

(54) METHOD FOR IMPROVING HUMAN BLOOD CIRCULATION

(76) Inventor: Alevtina Brady, Staten Island, NY (US)

( * ) Notice: Subject to any disclaimer, the term of this patent is extended or adjusted under 35 U.S.C. 154(b) by 363 days.

(21) Appl. No.: 12/390,436

(22) Filed: Feb. 21, 2009

(65) Prior Publication Data
US 2010/0215778 A1  Aug. 26, 2010

(51) Int. Cl.
*A61K 36/20* (2006.01)
*A61K 36/38* (2006.01)
*A61K 36/886* (2006.01)
*A61K 36/13* (2006.01)
*A61K 36/00* (2006.01)

(52) U.S. Cl. ........ 424/771; 424/730; 424/732; 424/744; 424/750; 424/770; 424/725; 424/774; 424/777; 424/778

(58) Field of Classification Search .................. None
See application file for complete search history.

(56) References Cited

U.S. PATENT DOCUMENTS

| | | |
|---|---|---|
| 1,710 A | 7/1840 | Warren |
| 113,894 A | 4/1871 | Kolestner |
| 579,580 A | 3/1897 | Holm |
| 1,092,699 A | 4/1914 | Depenbrock |
| 1,093,055 A | 4/1914 | Johnson |
| 1,464,093 A | 3/1923 | Friedlander |
| 2,326,035 A | 8/1943 | Jessup |
| 2,551,552 A | 5/1951 | Wahl |
| 2,858,547 A | 11/1958 | Baumann |
| 3,092,843 A | 6/1963 | Wright |
| 3,351,957 A | 11/1967 | Ikeda |
| 4,031,573 A | 6/1977 | Romanoff |
| 4,137,574 A | 2/1979 | Collins |
| 4,432,103 A * | 2/1984 | Hunziker .................. 4/525 |
| 5,050,251 A | 9/1991 | Pride |
| 5,416,931 A | 5/1995 | Wolfenden et al. |
| 6,086,853 A | 7/2000 | Michaels |
| 6,615,419 B1 | 9/2003 | Chang |
| 6,745,412 B1 | 6/2004 | Egeresi |
| 7,427,417 B2 | 9/2008 | Jendrucko |
| 2007/0020301 A1* | 1/2007 | Shimagami et al. .......... 424/401 |
| 2009/0112293 A1* | 4/2009 | Haslauer ................ 607/85 |
| 2010/0216891 A1* | 8/2010 | Shimono et al. ............ 514/675 |

FOREIGN PATENT DOCUMENTS

| | | | |
|---|---|---|---|
| CN | 101548855 | * | 10/2009 |
| KR | 2007012755 | * | 1/2007 |
| WO | WO2003055434 A1 | | 7/2003 |

* cited by examiner

*Primary Examiner* — Christopher R. Tate
(74) *Attorney, Agent, or Firm* — Alexey Bakman, Esq.

(57) ABSTRACT

The method of human prophylaxis comprising a number of steps is claim. First, the client is prepared for a steam bath, by applying a herbal paste on the skin, over at least one area of the client's body. The herbal paste is allowed to be absorbed into the client's body for an amount of time of at least five minutes and is followed with a massage the client's body. The client is then placed into a cedar steam barrel, connected to the steam generator, where the client's body is exposed to the steam. Following the stream procedure, the herbal paste is reapplied, the client's body is massaged, and the client to rests and drinks at least one cup of tea.

19 Claims, 1 Drawing Sheet

METHOD FOR IMPROVING HUMAN BLOOD CIRCULATION

FIELD OF THE INVENTION

The field of the present invention is prophylaxis methods and particularly a method of prophylaxis, involving the application of high temperatures, steam and herbs to a human body.

BACKGROUND OF THE INVENTION

As human body ages, blood vessels constrict and lose their elasticity. Deposits of cholesterol and/or toxic substances accumulate on the inner walls, restricting the flow through larger veins and arteries, and often completely blocking the flow through smaller capillaries. Such obstructions are exacerbated by the conditions of modern life—lack of exercise, unhealthy eating habits, environmental pollution, etc. Needless to say, such obstructions in the vessels decrease the blood flow and have an effect on functions of all the organs of the body. Obstacles in the circulatory system prevent the necessary nutrients and oxygen from reaching the heart, brain, and other vital organs, causing chronic diseases, accelerated aging of tissue and necrosis. Stuffed vessels also greatly increase the risk of instant death from stroke and related conditions.

Steam baths are often recommended as a kind of "vessel" gymnastics, forcing the vessels to expand and contract, thus somewhat restoring elasticity and clearing away some of the obstructions inside the vessels. Steam baths also improve the absorption and increase the efficiency of other treatment methods, such as herbal treatment.

Most such steam baths are applied in a sauna, where a person sits on a bench in a heated room. A steam generator is often positioned outside of the sauna and channels water steam, sometimes with herbal extracts into the room. However, the aggressiveness of such "hot room" therapy is limited. If the temperature or duration of a regular sauna treatment is exceeded, the overheating of client's head is likely to cause heat stroke and/or the loss of consciousness. Similarly, extended sauna time may lead to the irritation and burns of the respiratory system.

Herbal procedures may be used to clear away the obstructions in the circulatory system, as well as toxins and other foreign objects from the body. Often toxins, and other harmful substances in the body are of organic nature. Frequently their molecular composition is such that body by itself can not extract, destroy, or otherwise clear out the substances. The introduction of proper herbal substances into the body can often cause the toxins and other unwanted substances to chemically react with the herbal substances and thus change chemical structure of harmful particles, making them excretable by the body.

Herbal therapy may be applied externally, so that it absorbs into the body tissues through the skin, or breathed in by a client. However, when applied externally, the absorption through the skin into the body is minimal. Herbal steam baths do increase the rate of absorption through the skin by opening the pores and dilating the blood vessels. However, as described above, the duration and temperature of such procedures has to be greatly limited due to the possible overheating of the central nervous system and the sensitivity of respiratory system.

Therefore, there is a long-standing and unfulfilled need in the art for a method of human prophylaxis and body cleansing that would combine and maximize the benefits of the combined steam room and herbal treatment. This method should allow for better absorption of herbal therapy through the use of steam, without the risk of burns or overheating of the Central Nervous System. There is also a need for a functional combination of herbs that would be effective at cleansing and otherwise rejuvenating, strengthening and curing the body and that could be used most beneficially in combination with the steam therapy. The present invention achieves these objectives and provides numerous other benefits.

SUMMARY OF THE PRESENT INVENTION

The present invention is defined by the following claims and nothing in this section should be taken as a limitation on those claims.

The invention describes and claims method of human prophylaxis. The method comprises the plurality of steps. The client is first prepared for a steam bath. The preparation involves the application of a herbal paste on the skin, over at least one area of the client's body. The herbal paste is then allowed to absorb into the client's body for an amount of time of at least five minutes. The client's body is then subjected to a massage.

The client is then placed into a cedar steam barrel. The cedar steam barrel comprises an inner steaming compartment and a head hole, positioned in an upper half of the cedar steam barrel. The head hole is intended for allowing the client to keep client's head above the inner steaming compartment.

The steam barrel is connected to the steam generator, which is intended for pumping steam into the steam barrel. The client's body is exposed to the steam inside of the inner steaming compartment. The client is then taken out of the inner steaming compartment.

As the next step, the herbal paste is reapplied to the client's body, while he or she receives another massage. The client is allowed to rest in warm environment for at least 5 minutes, and preferably longer, while drinking at least one cup of tea.

DETAILED DESCRIPTION OF THE PREFERRED EMBODIMENTS

Figure 1:
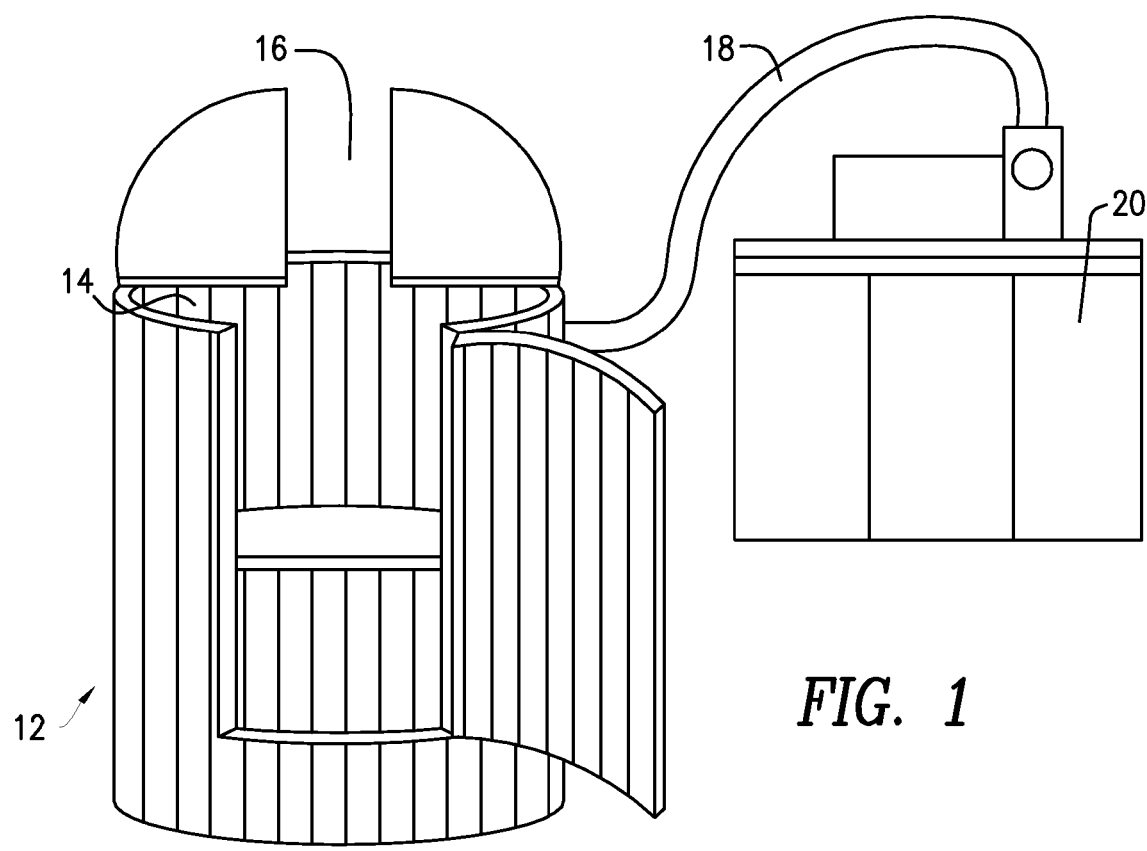
FIG. 1 is a perspective view of one of the preferred embodiments of the cedar steam barrel and steam generator for use in the method of the present invention.
Figure 2:
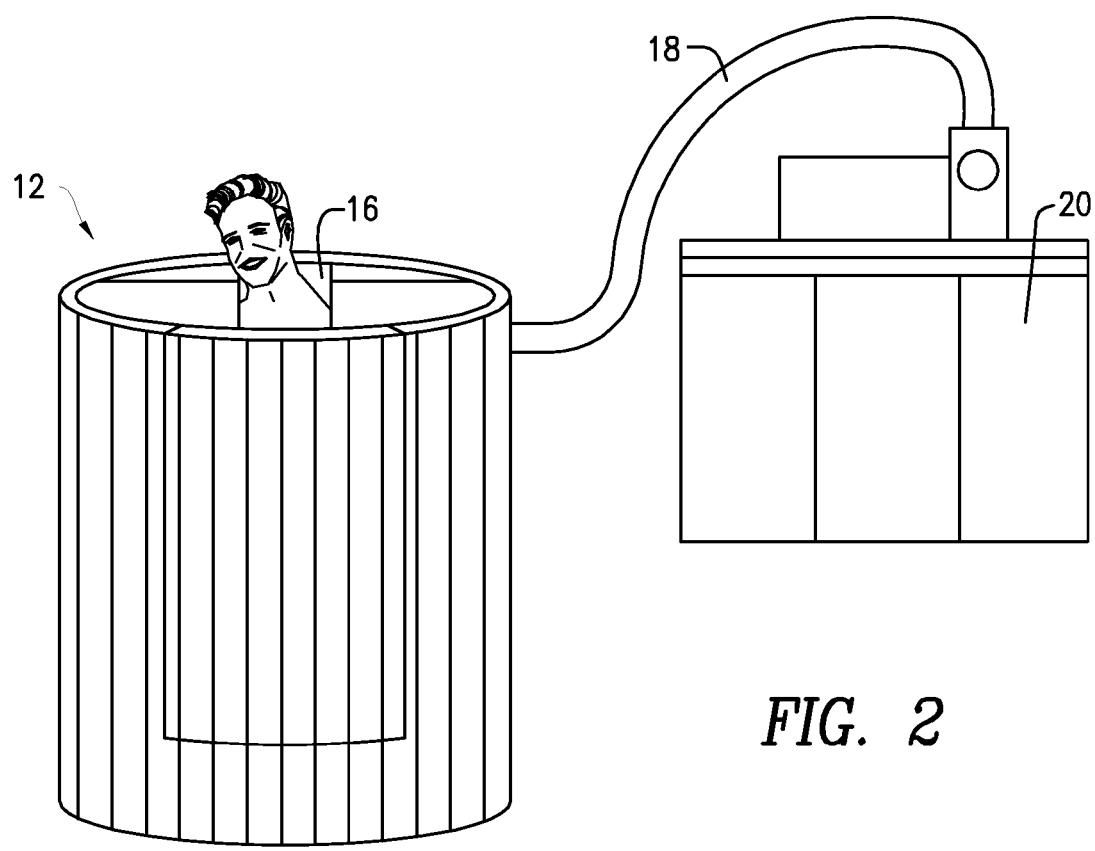
FIG. 2 is a perspective view of one of the preferred embodiments of the cedar steam barrel and steam generator for use in the method of the present invention, showing the barrel in use.

The method of the present invention will now be illustrated in detail, with reference to the accompanying drawings.

Present invention discloses a method of human prophylaxis, incorporating the use of the special barrel-type sauna 12 (also referred to as barrel 12) with particular method of application of specific herbal composition, to achieve positive results in prophylaxis of cardiovascular functions, kidney malfunction, common colds, muscle and joint pains, rheumatoid arthritis, immune system deterioration, and chronic fatigue syndrome, among other conditions.

The first step of the method involves the application of an herbal paste on the skin, over at least one area of the client's body. If a client complains of a preexisting condition or pain, then preferably, the herbal paste is placed over the skin, directly over, or as close to the trouble spots as possible. In some embodiments, particularly where the procedure is carried out purely for the purpose of prophylaxis, the herbal paste is applied over most of the surface of the client's body.

In the preferred embodiment of the invention, the herbal paste comprises at least oak bark, maple leaves, bamboo leaves, poplar leaves, and willow leaves. Preferably, all of these ingredients are taken in roughly equal proportions by weight, and finely chopped, (if dry, preferably into a powdery substance). Preferably, the herbs are taken in dried-out state. Generally, finer size of the particles is preferred, as that will improve absorption of the paste through the skin. The chopped/crushed/pulverized ingredients are then mixed with sufficient amounts of a liquid substance, to form a (preferably) thick paste. Preferably, the liquid substance is simple water. However, in some embodiments, it can be an absorbent cream, to facilitate the passing of the herbal paste through the skin.

In some embodiments of the present invention, the herbal paste further comprises (the leaves of) aloe, berries of red bilberry, leaves of red bilberry, red clover (whole), nettle (preferably leaves), burdock (preferably leaves), dandelion (preferably whole), currant (preferably leaves), and celandine (preferably whole). In yet other variants of the invention, the herbal paste further comprises birch (preferably a mixture of buds and leaves), hawthorn (preferably a mixture of berries and leaves), oregano leaves, raspberry leaves, raspberry berries, coltsfoot leaf, plantain leafs, wormwood (preferably leaves), motherwort (preferably leaves), chamomile (preferably whole), mountain ash (preferably leaves), currant leaves, pine needles, comsilk, milfoil, dill, tickseed, Saint-John's-wort, linden flowers, bird cherry, dog rose flowers. Again, these herbs should preferably be pulverized or ground up into the particle size fine enough to create a paste, when mixed with water. In the preferred embodiments of the method of the present invention, the paste also comprises one or more of the following elements: bee honey, propolis, royal jelly, beeswax, bee venom (apitoxin), apple vinegar, seaweed. Preferably, all of the latter elements are present.

Once the herbal paste is applied to the client's skin, it should be allowed to absorb into the client's body for an amount of time of at least five minutes and at most, an hour. Preferably, however, the herbal paste is allowed to absorb into the client's body for the amount of time between 10 and 20 minutes.

Following the application of the herbal paste, client's body is massaged, preferably while the herbal paste is still on the client's body. This allows for better circulation of the blood, and thus better absorption of the herbal paste into the body. Furthermore, this massage "warms up" the body and the vessels for the heat stress of the cedar steam barrel.

Following the massage, the herbal paste is preferably washed off from the client's body. The washing off does not need to be thorough, so that some remnants of the herbal paste may continue to absorb into the body once the client is inside of the steam barrel. In some non-preferred variants of the method of the present invention, the client enters the steam barrel with herbal paste still on the body.

The client is then placed into a cedar steam barrel 12. The cedar steam barrel 12 comprises an inner steaming compartment 14 and a head hole 16. The head hole is positioned in an upper half of the cedar steam barrel, and is intended for allowing the client to keep his or her head above the inner steaming compartment. Keeping the client's head out of the cedar steam barrel (otherwise referred to as the sauna box, or the barrel) allows for longer durations and higher temperatures in the inner steaming compartment, without overheating the client's head or burning the client's lungs and mucous membranes. Although any shape sauna box with the head hole may be used for the present method, a cylindrical shape steam barrel is preferred.

Although the barrel (sauna box) with a head-hole, required for the present method, can be made of several different types of wood, and even resins and other artificial materials, cedar wood is strongly preferred. Cedar wood produces natural oil and extracts that are natural preservatives for the wood against attacks by insects and decay-causing fungi. Cedar wood oil is also known among herbalists for its bactericidal and disease-curing properties. It also exhibits low shrinkage and good heat retention, and is thus the preferred choice for the prophylaxis method of the present invention.

The steam barrel 12 is connected (preferably through a flexible heat-resistant hose 18) to the external steam generator 20. The steam generator 20 is intended for pumping steam into the steam barrel 12. Numerous types of steam generators 20 are available commercially for small saunas and sauna boxes and are well known to those skilled in the art. Many of such steam generators 20 allow for herbal extracts to be added into the generator for production of steam with essence of the added herbs. Preferably, such steam generators 20, allowing for addition of herbs into the steam, are used in the present method. One preferred device for use as an external steam generator is a Russian-made steam generator, currently distributed under the trademark PG-3 ("Parogenerator") by Progress 7 Corporation.

Once inside of the barrel 12, the client's body is exposed to the steam inside of the inner steaming compartment 14. The time and temperature of exposure must be determined by the client's age, health condition, and comfort level. The preferred steaming time for most clients is 10-15 minutes at the temperature of 90-110 degrees Fahrenheit. The client is then taken out of the inner steaming compartment 14.

In the preferred embodiment, the herbal paste is reapplied to the client's body as soon as the client is out of the inner steaming compartment 14 of the barrel 12. Preferably, the herbal paste is reapplied to most (over 50 percent) of the surface of the client's body, although in other embodiments the paste is applied only to the places near the area of a disorder. It is preferable if the herbal paste, is heated to above the room temperature.

The client's body is then again massaged. The massage is followed by the client resting and drinking at least one cup of hot tea. Preferably, the at least one cup of hot tea is two or more cups of hot tea, in order to replenish the water lost from the client's body through perspiration. Preferably the tea is an herbal tea, with at least one of the ingredients being the same as the ingredients of the herbal paste.

Following the massage, the client is allowed to rest in warm environment for at least 5 minutes. The tea is preferably taken by the client while the client is relaxing in the warm environment. In the preferred embodiments of the method, during the relaxation, the client's body is covered with a warm cloth, such as a terry towel for at least ten minutes, following the reapplication of the herbal paste to the client's body and massaging the client's body.

As stated above, the steam pumped into the cedar steam barrel 12 from the steam generator 20 is preferably saturated with the smell of herbs, contained in the steam generator. The term "smell," as used in this description and the claims refers to microscopic aromatic oils and particles of the herbs, suspended in the vapor, which can be breathed in by the client. In the preferred embodiment of the invention, the steam comprises the smell of at least the following herbs contained in the steam generator: oak bark, maple leaves, bamboo leaves, poplar leaves, and willow leaves. These are the same herbs present in the herbal paste. Preferably, these herbs are placed into the steam generator in roughly equal proportions.

In some preferred embodiments of the invention, the steam pumped into the cedar steam barrel further comprises the smell of all or some of the additional herbs contained in the steam generator: aloe, berries of red bilberry, leafs of red bilberry, red clover, nettle, burdock, dandelion, currant, and celandine. In yet other embodiments of the invention, all or some of the following herbs can be used in the steam generator: birch, hawthorn, oregano leaves, raspberry leaves, raspberry berries, coltsfoot leaf, plantain leafs, wormwood, motherwort, chamomile, mountain ash, currant leaves, pine needles, corn silk, milfoil, dill, tickseed, Saint-John's-wort, linden flowers, bird cherry and dog rose flowers.

In some alternative embodiments, the exact combination of oak bark, maple leaves, bamboo leaves, poplar leaves, and willow leaves is not required, and the herbs may be selected from the group consisting of oak bark, maple leaves, bamboo leaves, poplar leaves, willow leaves, aloe, berries of red bilberry, leafs of red bilberry, red clover, nettle, burdock, dandelion, currant, celandine, birch, hawthorn, oregano leaves, raspberry leaves, raspberry berries, coltsfoot leaf, plantain leafs, wormwood, motherwort, chamomile, mountain ash, currant leaves, pine needles, cornsilk, milfoil, dill, tickseed, Saint-John's-wort, linden flowers, bird cherry and dog rose flowers. The combination comprising aloe, berries of red bilberry, and leafs of red bilberry, and the combination comprising red clover, nettle, burdock, dandelion, currant, and celandine may also be used in alternative embodiments.

It is to be understood that while the apparatus and method of this invention have been described and illustrated in detail, the above-described embodiments are simply illustrative of the principles of the invention and the forms that the invention can take, and not a definition of the invention. It is to be understood also that various other modifications and changes may be devised by those skilled in the art which will embody the principles of the invention and fall within the spirit and scope thereof. It is not desired to limit the invention to the exact construction and operation shown and described. The spirit and scope of this invention are limited only by the spirit and scope of the following claims.

I claim:

1. A method for improving human blood vessel circulation comprising the steps of:
   a. preparing a client for a steam bath, the preparation comprising the steps of:
      i. applying a herbal paste on the skin, over at least one area of the client's body,
      ii. allowing the herbal paste to absorb into the client's body for an amount of time of at least five minutes and at most, an hour;
      iii. massaging the client's body;
   b. placing the client into a cedar steam barrel,
      i. wherein the cedar steam barrel comprises an inner steaming compartment and a head hole, said head hole positioned in an upper half of the cedar steam barrel, and wherein the head hole is intended for allowing the client to keep the client's head above the inner steaming compartment,
      ii. and wherein said steam barrel is connected to a steam generator, said steam generator pumping steam into the steam barrel;
      iii. exposing the client's body to the steam inside of the inner steaming compartment,
      iv. taking the client out of the inner steaming compartment
   c. reapplying the herbal paste to the client's body
   d. massaging the client's body,
   e. allowing the client to rest in warm environment for at least 5 minutes,
   f. drinking, by the client, of at least one cup of tea;
   wherein the herbal paste comprises at least one herb, selected from the group consisting of oak bark, maple leaves, bamboo leaves, poplar leaves, willow leaves, aloe, berries of red bilberry, leafs of red bilberry, red clover, nettle, burdock, dandelion, currant, celandine, birch, hawthorn, oregano leaves, raspberry leaves, raspberry berries, coltsfoot leaf, plantain leafs, wormwood, motherwort, chamomile, mountain ash, currant leaves, pine needles, cornsilk, milfoil, dill, tickseed, Saint-John's-wort, linden flowers, bird cherry, and dog rose flowers, and mixtures thereof.

2. A method for improving human blood vessel circulation comprising the steps of:
   a. preparing a client for a steam bath, the preparation comprising the steps of:
      i. applying a herbal paste on the skin, over at least one area of the client's body,
      ii. allowing the herbal paste to absorb into the client's body for an amount of time of at least five minutes and at most, an hour;
      iii. massaging the client's body;
   b. placing the client into a cedar steam barrel,
      i. wherein the cedar steam barrel comprises an inner steaming compartment and a head hole, said head hole positioned in an upper half of the cedar steam barrel, and wherein the head hole is intended for allowing the client to keep the client's head above the inner steaming compartment,
      ii. and wherein said steam barrel is connected to a steam generator, said steam generator pumping steam into the steam barrel;
      iii. exposing the client's body to the steam inside of the inner steaming compartment,
      iv. taking the client out of the inner steaming compartment
   c. reapplying the herbal paste to the client's body
   d. massaging the client's body,
   e. allowing the client to rest in warm environment for at least 5 minutes,
   f. drinking, by the client, of at least one cup of tea;
   wherein the herbal paste comprises a combination of herbals selected from the group consisting of oak bark, maple leaves, bamboo leaves, poplar leaves, and willow leaves.

3. The method of claim 2, wherein the cedar steam barrel is of cylindrical shape, and wherein the steam pumped into the cedar steam barrel from the steam generator is saturated with aromas of herbs, said herbs contained in the steam generator, and wherein the at least one cup of tea refers to at least one cup of herbal tea.

4. The method of claim 3, wherein the herbal paste further comprises a combination of herbals selected from the group consisting of aloe, berries of red bilberry, leafs of red bilberry, red clover, nettle, burdock, dandelion, currant, and celandine.

5. The method of claim 4, wherein the herbal paste further comprises a combination of herbals selected from the group consisting of birch, hawthorn, oregano leaves, raspberry leaves, raspberry berries, coltsfoot leaf, plantain leafs, wormwood, motherwort, chamomile, mountain ash, currant leaves, pine needles, cornsilk, milfoil, dill, tickseed, Saint-John's-wort, linden flowers, bird cherry, and dog rose flowers.

6. The method of claim 3, wherein the steam pumped into the cedar steam barrel comprises the aromas of at least the following herbs, said herbs contained in the steam generator: oak bark, maple leaves, bamboo leaves, poplar leaves, and willow leaves.

7. The method of claim 6, wherein in the step of preparing the client for a steam bath, the herbal paste is allowed to absorb into the client's body for the amount of time between 10 and 20 minutes.

8. The method of claim 7, wherein in the step of preparing the client for a steam bath, the herbal paste is applied over most of the surface of the client's body.

9. The method of claim 8, wherein in the step of preparing the client for a steam bath further comprises a step of washing off the herbal paste from the client's body, prior to the step of placing the client into a cedar steam barrel.

10. The method of claim 9, wherein all of the herbs in the herbal paste are mixed in equal proportions.

11. The method of claim 10, further comprising a step of covering the client's body with a warm cloth for at least ten minutes, following the reapplication of the herbal paste to the client's body and massaging the client's body.

12. The method of claim 6, wherein the steam pumped into the cedar steam barrel further comprises the aromas of the following herbs, said herbs contained in the steam generator: aloe, berries of red bilberry, leafs of red bilberry, red clover, nettle, burdock, dandelion, currant, and celandine.

13. The method of claim 12, wherein the steam pumped into the cedar steam barrel further comprises the aromas of the following herbs, said herbs contained in the steam generator: birch, hawthorn, oregano leaves, raspberry leaves, raspberry berries, coltsfoot leaf, plantain leafs, wormwood, motherwort, chamomile, mountain ash, currant leaves, pine needles, cornsilk, milfoil, dill, tickseed, Saint-John's-wort, linden flowers, bird cherry, and dog rose flowers.

14. The method of claim 2, wherein the herbal paste comprises aloe, berries of red bilberry, and leafs of red bilberry.

15. The method of claim 2, wherein the herbal paste comprises red clover, nettle, burdock, dandelion, currant, and celandine.

16. The method of claim 3, wherein the herbal paste further comprises bee honey.

17. The method of claim 3, wherein the herbal paste further comprises, propolis, royal jelly, beeswax and bee venom.

18. The method of claim 3, wherein the herbal paste further comprises apple vinegar.

19. The method of claim 3, wherein the herbal paste further comprises seaweed.

* * * * *